United States Patent
Bloem

(10) Patent No.: US 7,171,962 B1
(45) Date of Patent: Feb. 6, 2007

(54) SOFT ORAL AIRWAY FOR INTRAVENOUS ANESTHESIA AND METHOD OF USE

(76) Inventor: Gloria Turner Bloem, 154 S. Lewis St., Newport, NC (US) 28570

(*) Notice: Subject to any disclaimer, the term of this patent is extended or adjusted under 35 U.S.C. 154(b) by 0 days.

(21) Appl. No.: 11/036,570

(22) Filed: Jan. 14, 2005

(51) Int. Cl.
A61M 16/00 (2006.01)

(52) U.S. Cl. ............................ 128/200.26; 128/207.14

(58) Field of Classification Search ............. 128/848, 128/859, 860, 861, 863, 200.24, 200.26, 128/206.29, 207.14, 207.15, 207.16, 207.18; 600/237, 238; 606/108, 191, 196, 199
See application file for complete search history.

(56) References Cited

U.S. PATENT DOCUMENTS

| 3,306,298 | A | * | 2/1967 | Raimo | 128/207.14 |
| 3,508,543 | A | * | 4/1970 | Aulicono | 128/202.28 |
| 3,543,751 | A | * | 12/1970 | Sheffer | 128/207.15 |
| 3,930,507 | A | * | 1/1976 | Berman | 128/207.14 |
| 3,951,136 | A | | 4/1976 | Wall | |
| 4,112,936 | A | * | 9/1978 | Blachly | 128/861 |
| 4,651,746 | A | * | 3/1987 | Wall | 600/483 |
| 4,715,379 | A | * | 12/1987 | McCormick | 606/234 |
| 4,815,459 | A | * | 3/1989 | Beran | 128/207.14 |
| 4,919,126 | A | * | 4/1990 | Baildon | 128/207.14 |
| 5,205,281 | A | * | 4/1993 | Buchanan | 128/207.14 |
| 5,273,032 | A | * | 12/1993 | Borody | 128/207.14 |
| 5,355,874 | A | * | 10/1994 | Bertram | 128/200.26 |
| 5,393,787 | A | | 2/1995 | Price | |
| 5,413,095 | A | * | 5/1995 | Weaver | 128/200.26 |
| 5,443,063 | A | | 8/1995 | Greenberg | |
| 5,513,634 | A | * | 5/1996 | Jackson | 128/207.18 |
| 5,743,258 | A | | 4/1998 | Sato et al. | |
| 6,098,617 | A | * | 8/2000 | Connell | 128/200.26 |
| 6,135,111 | A | | 10/2000 | Mongeon | |
| 6,196,224 | B1 | | 3/2001 | Alfrey | |
| 6,374,824 | B1 | | 4/2002 | Thorton | |
| 6,386,199 | B1 | | 5/2002 | Alfrey | |
| 6,390,093 | B1 | | 5/2002 | Mongeon | |
| 6,533,984 | B2 | * | 3/2003 | Curti | 264/219 |
| 6,568,388 | B2 | * | 5/2003 | Christopher | 128/200.26 |
| 6,729,325 | B2 | | 5/2004 | Alfrey | |
| 2003/0131853 | A1 | * | 7/2003 | Wall et al. | 128/207.14 |
| 2004/0154623 | A1 | * | 8/2004 | Schaeffer et al. | 128/207.14 |

\* cited by examiner

Primary Examiner—Teena K. Mitchell
(74) Attorney, Agent, or Firm—Olive & Olive, P.A.

(57) ABSTRACT

A soft oral airway comprising an elongate hollow tubular member having a proximal and a distal end, wherein the member comprises a soft flexible material and an opening at the distal end of the elongate tubular member for insertion into the mouth and pharynx of a patient with the distal end leading the member as the member is inserted into the mouth and pharynx of a patient and an enlarged tapered opening at the proximal end, wherein the enlarged opening is dimensioned to not slip down the throat of the patient and the opening at the proximal end is adapted to receive a nasal cannula.

10 Claims, 2 Drawing Sheets

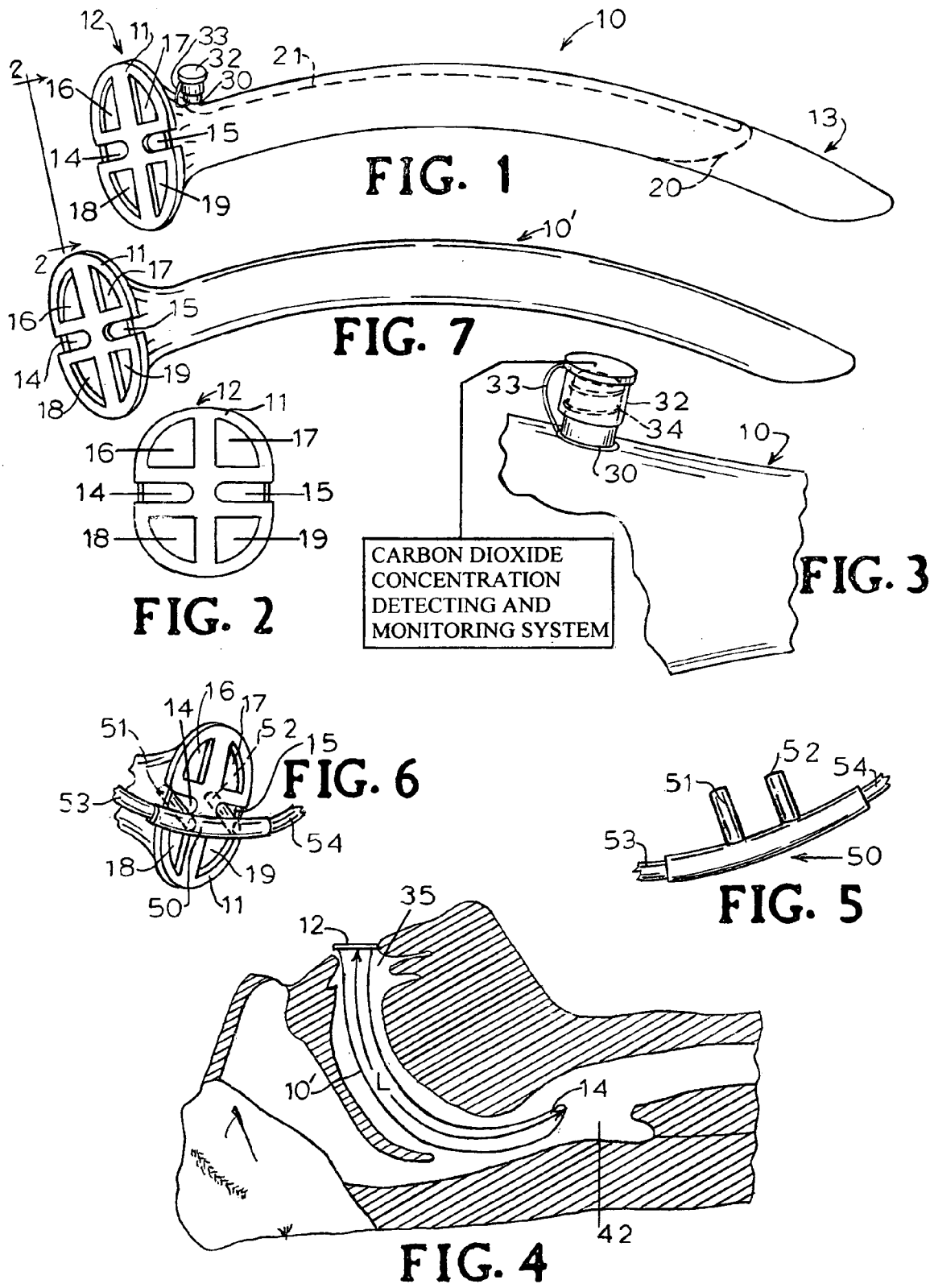

SOFT ORAL AIRWAY FOR INTRAVENOUS ANESTHESIA AND METHOD OF USE

FIELD OF THE INVENTION

The present invention relates generally to a class of medical devices commonly referred to as oral airways, by which term is meant a medical device used to both establish and protect an oral airway between the mouth and pharynx of the patient. More specifically, the present invention is directed to a soft oral airway that serves as a flexible airway support for use in patients under intravenous sedation and, in one embodiment, is constructed so as to facilitate monitoring of the patient during sedation.

BACKGROUND OF THE INVENTION

All persons in good health breathe through a natural airway. However, under sedation, some patients require support of their airway by the use of a device referred to as an oral airway. Oral airways are sometimes used in patients undergoing sedation by anesthesia to provide an airway from the mouth to the pharynx. The typical oral airway is made of a hard plastic, however the disadvantage of such typical oral airway is that it is uncomfortable. The use of a typical hard plastic airway is nevertheless sometimes used with intravenous sedation, during which the patient is breathing on his or her own, and does not need an endotracheal tube.

Most known oral airways, as mentioned above, are comprised of a hard plastic material throughout their length with no variation in softness. Most known oral airways comprise a hard plastic material in order to achieve their function of keeping the tongue and soft tissue of the pharynx out of the way to prevent occlusion of the airway.

The presently known hard plastic oral airways can present problems particularly when used in patients undergoing intravenous sedation, in which the patient is breathing on his or her own. For example, since the hard plastic material is uncomfortable, it can cause a gag reflex, whenever the patient is less sedated.

Due to the limitations of hard plastic oral airways, there is a need in the field for a more comfortable oral airway to provide oxygen flow or airway exchange to a patient particularly when undergoing intravenous sedation.

BRIEF DESCRIPTION OF THE DRAWINGS

FIG. 1 is a perspective view of the soft, oral airway member of the present invention with an optional carbon dioxide monitoring tube and optional scoring.

FIG. 2 is an end view of the enlarged opening of the proximal end of the soft oral airway member taken in the direction of line 2—2 of FIG. 1.

FIG. 3 is an enlarged, fragmentary perspective view of a portion of the proximal end of the soft oral airway member of the invention and showing an opening for a carbon dioxide monitoring tube, a tube mounted in the opening and corresponding tethered cap.

FIG. 4 is a cross-sectional side view of the mouth and throat area of a patient illustrating the soft oral airway member of the invention (constructed in the form shown in FIG. 7) inserted into the patient's mouth and pharynx.

FIG. 5 is a fragmentary perspective view of a nasal cannula of a type suited for use with the soft oral airway member of the invention.

FIG. 6 is a fragmentary perspective view illustrating the nasal cannula of FIG. 5 positioned in the proximal end of the soft oral airway member of the invention.

FIG. 7 is a perspective view of the soft oral airway member of the invention, but without the carbon dioxide monitoring tube and scoring shown in FIG. 1.

DETAILED DESCRIPTION

Figure 8:
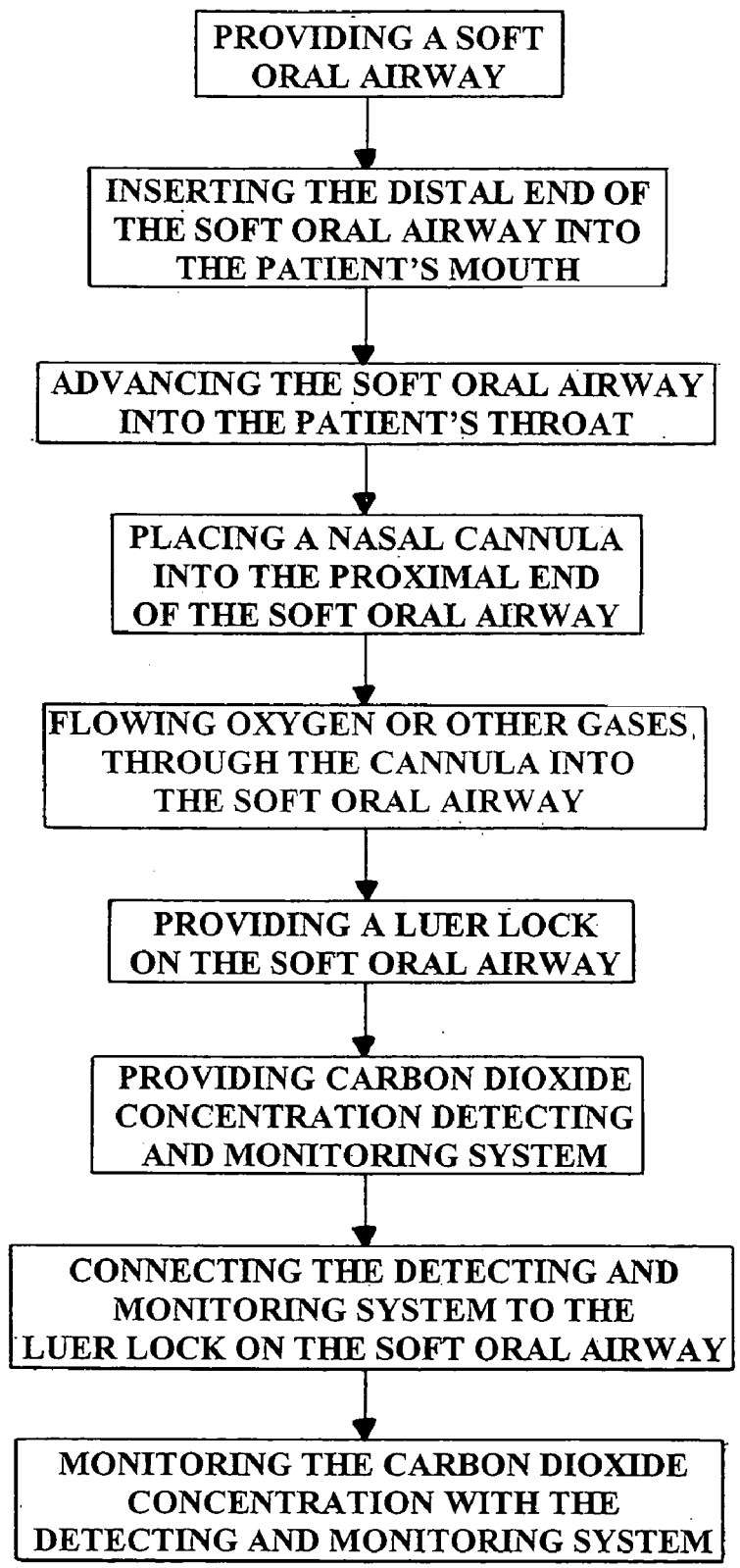
FIG. 8 is a flow chart of the method of use of the soft oral airway of the invention, according to one embodiment.

Referring now to FIG. 1, there is shown a perspective view of a soft oral airway member 10 formed with an optional carbon dioxide monitoring tube and optional scoring in accordance with the instant invention. Member 10 has a proximal end 12 and a distal end 13. Proximal end 12 is outwardly tapered, which serves to prevent member 10 from advancing down the patient's throat. Proximal end 12 mounts plate 11, which has two slotted openings 14 and 15 dimensioned to receive two prongs 51 and 52 (FIG. 5) of a nasal cannula 50, discussed later. Slotted openings 14 and 15 also permit the introduction of a nasal catheter. Plate 11 on proximal end 12 also has one or more holes 16, 17, 18, and 19 to permit air exchange. Member 10 is formed of a soft flexible material such as silicone or other soft flexible material such as soft plastic or soft tygon tubing. Distal end 13 may, if desired, have scoring 20 around the circumference of member 10 to permit easy cutting, allowing a shorter length to be obtained. An optional carbon dioxide monitoring tube 21 is shown running the length of the inner wall of member 10 and protruding through an opening 30 in the wall of member 10. Tube 21 is shown with a cap 32 secured by a tether 33.

FIG. 2 shows an end view of the enlarged proximal end 12 of the soft oral airway member 10. Plate 11 on the proximal end 12 has, as previously mentioned, two slotted openings 14 and 15 to receive the two prongs 51 and 52 (FIG. 5) of the nasal cannula 50. The slotted openings 14 and 15 also permit the introduction of a nasal catheter. The proximal end 12 also has one or more holes 16, 17, 18, and 19 to permit air exchange.

FIG. 3 shows an enlarged fragmentary perspective view of opening 30 for carbon dioxide monitoring tube 21 and its corresponding cap 32 and tether 33. Tube 21 protrudes through opening 30 in the wall of member 10 where member 10 tapers outwardly to the proximal end 12. Tether 33 prevents accidental loss of cap 32. Opening 30 optionally provides a luer lock mechanism 34, shown in dashed lines.

FIG. 4 shows, in a cross-sectional side view, the mouth and throat area of a patient using soft oral airway member 10, constructed according to FIG. 7, inserted into the mouth of the patient. Enlarged proximal end 12 is shown positioned just outside the patient's mouth 35. Length L of member 10 is made such that distal end 13 of member 10 reaches the pharynx 42 of the patient, but no further.

FIG. 5 shows a fragmentary perspective view of a nasal cannula 50 of a type suited for use with the soft oral airway member 10 of the invention. Nasal cannula 50 has prongs 51 and 52 that are usually inserted in a patient's nostrils to provide a source of oxygen, air, or other gases. The oxygen is fed into nasal cannula 50 by tubes 53 and 54 on either side.

FIG. 6 shows a fragmentary perspective view of nasal cannula 50 positioned in plate 11 on proximal enlarged end 12 of the invention. Prongs 51 and 52 (FIG. 5) insert into slotted openings 14 and 15 to provide oxygen that will flow through the interior of the member 10 to a patient's lungs.

FIG. 7 shows a perspective view of soft oral airway member 10' in accordance with an embodiment of the instant invention without the optional carbon dioxide monitoring tube 21 or the optional scoring 20.

FIG. 8 is a flow chart of the method of using the invention, according to one embodiment. The method of using member 10 to provide a soft oral airway member 10 to a patient undergoing intravenous anesthesia sedation comprises providing a soft oral airway member 10 to a patient, inserting the soft oral airway member 10 into the mouth of the patient wherein distal end 13 is first inserted. Soft oral airway member 10 is axially advanced into the mouth of the patient until distal end 13 reaches pharynx 42 of the patient, or until adequate air exchange has been achieved with the lungs. Prongs 51 and 52 of nasal cannula 50 are inserted into slotted openings 14 and 15 of proximal enlarged end 12 of oral airway member 10. Oxygen flows into nasal cannula 50 by way of tubes 53 and 54. Oxygen or other gases flow through prongs 51 and 52 of nasal cannula 50 and into proximal enlarged end 12 at slotted openings 14 and 15, through the hollow interior of soft oral airway member 10 and exits distal end 13 to be available to the patient.

Carbon dioxide levels of the patient are monitored by commercially available carbon dioxide concentration detecting and monitoring systems as are commonly known in the field. These systems connect to the opening at proximal end 12, that optionally further comprises a luer lock (shown by dashed lines in FIG. 3), located at the end of tube 21 underneath cap 32. Tube 21 provides a route for monitoring carbon dioxide concentrations without interfering with the interface of nasal cannula 50 with proximal enlarged end 12 of soft oral airway member 10. Preferably, tube 21 will extend towards distal end 13 short of reaching scoring 20 so that oral airway member 10 can be more easily cut to a desired length, without having to also cut tube 21.

Member 10 can be of any suitable length, but is preferably 13, 14, or 15 centimeters long. The diameter of member 10 can be of any suitable diameter for the patient, but is preferably either 1.0, 1.5 or 1.4 centimeters in diameter. The thickness of the wall of member 10 can be of any suitable thickness, but is preferably either 1.0, 1.5, or 2.0 millimeters thick. Member 10 can be straight or curved, but preferably will have a curvature as shown in FIG. 1.

The present invention provides distinct advantages over the known art by allowing a less intrusive and stimulating oral airway member to be inserted through the patient's mouth into the pharynx to provide oxygen or other gases to a patient undergoing intravenous anesthesia. The soft oral airway member of the present invention is comprised of a soft, flexible material, such as silicone, which does not agitate or stimulate a patient who is undergoing intravenous anesthesia procedures like a traditional hard plastic oral airway. Upon revival from the effects of anesthesia and removal of the soft oral airway member, the patient should not experience the discomfort associated with use of a hard plastic oral airway. Still further, the same nasal cannula initially placed in the nostrils of the patient to provide oxygen or other gases to the patient can be used with the soft oral airway member to provide oxygen or other gases to the oral pharynx and ultimately the lungs of the patient.

The foregoing is illustrative of the principles of the invention. However, since modifications and changes may be apparent to one skilled in the art, it is not desired to limit the invention to the exact construction shown and described with it being considered that all suitable modifications and equivalents are in fact within the scope of the claimed invention.

I claim:

1. A soft oral airway comprising:
   an elongate hollow tubular member formed of a soft flexible material and having a proximal and a distal end;
   an opening at said distal end of said elongate tubular member for insertion into the mouth and pharynx of a patient with said distal end leading said member as said member is inserted into the mouth and pharynx of a patient; and
   an enlarged tapered opening at said proximal end, dimensioned so as to not slip down the throat of said patient and said opening at said proximal end further comprising two slotted openings adapted to receive prongs of a nasal cannula, whereby oxygen being introduced thru said cannula flows thru the interior and said member to a patient's lungs.

2. The soft oral airway of claim 1, further comprising circular scoring around a perimeter of said distal end of said member, wherein said member may be easily cut to shorten said member.

3. The soft oral airway of claim 1, wherein said member comprises silicone.

4. The soft oral airway of claim 1, wherein said opening at said proximal end is formed of a plastic material.

5. The soft oral airway of claim 1, further comprising a tube of smaller diameter than said member and contained within the interior of said member, said tube extending between said distal and proximal ends of said member and at said proximal end extending radially outward and protruding through an inner wall of said member.

6. The soft oral airway of claim 5, wherein said tube is fitted with a luer lock at an outer end of said tube where said tube protrudes from said inner wall of said member.

7. A method for providing a soft oral airway for a patient undergoing intravenous sedation comprising:
   providing a soft, flexible, elongated hollow tubular member, having a distal end and an enlarged tapered head at a proximal end for insertion into the mouth and pharynx of a patient with the proximal end of said tubular member extending from the mouth of said patient, said proximal end further comprising two slotted openings adapted to receive prongs of a nasal cannula, whereby oxygen being introduced thru said cannula flows thru the interior and said member to a patient's lungs;
   inserting said distal end of said member into the mouth of said patient;
   axially advancing said member into the mouth of said patient until said distal end is positioned within the pharynx of said patient; and
   inserting a nasal cannula into slots in the proximal end of said member adapted to receive said cannula.

8. The method of claim 7, further comprising flowing oxygen through said cannula into said member, wherein said oxygen is available to the patient.

9. The method of claim 7, further comprising providing a tube of smaller diameter than said member formed on an inner wall of said member, wherein said tube extends from said distal end of said member to said proximal end of said member and extending radially outward and protruding through said inner wall of said member at said proximal end.

10. The method of claim 9, further comprising connecting carbon dioxide concentration detecting and monitoring system to a luer lock located at an end of said tube that protrudes from said proximal end of said oral airway member; and monitoring said carbon dioxide concentration with said detecting and monitoring system.

* * * * *